US00PP28508P3

(12) United States Plant Patent
Geers

(10) Patent No.: US PP28,508 P3
(45) Date of Patent: Oct. 10, 2017

(54) ***SPIRAEA* PLANT NAMED 'ODESSA'**

(50) Latin Name: *Spiraea japonica*
Varietal Denomination: Odessa

(71) Applicant: Herman Geers, Boskoop (NL)

(72) Inventor: Herman Geers, Boskoop (NL)

( * ) Notice: Subject to any disclaimer, the term of this patent is extended or adjusted under 35 U.S.C. 154(b) by 0 days.

(21) Appl. No.: 15/330,087

(22) Filed: Aug. 3, 2016

(65) Prior Publication Data

US 2017/0042074 P1 Feb. 9, 2017

Related U.S. Application Data

(60) Provisional application No. 62/282,642, filed on Aug. 6, 2015.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Audrey Charles

(57) ABSTRACT

A new and distinct cultivar of *Spiraea* plant named 'Odessa', characterized by its deep rosy-pink colored flowers, dark green-colored foliage, and moderately vigorous, compact-globular growth habit, is disclosed.

1 Drawing Sheet

CROSS-REFERENCE TO RELATED APPLICATIONS

This application claims the benefit of U.S. Provisional Application No. 62/282,642 filed Aug. 6, 2015.

Latin name of genus and species of plant claimed: *Spiraea japonica.*

Variety denomination: 'Odessa'.

BACKGROUND OF THE INVENTION

The present invention relates to a new and distinct cultivar of *Spiraea* plant botanically known as *Spiraea japonica* and hereinafter referred to by the cultivar name 'Odessa'.

The new cultivar originated in a controlled breeding program in Boskoop, The Netherlands during the summer of 2005. The objective of the breeding program was the development of *Spiraea* cultivars that have rich flower colors and a more compact growth habit useful for small hedges or mass plantings.

The new *Spiraea* cultivar is the result of cross-pollination. The female (seed) parent of the new cultivar is 'Little Princess', not patented, characterized by its light pink-colored flowers, medium green colored foliage, compact-globular growth habit. The male (pollen) parent of the new cultivar is 'Bullata', not patented, characterized by its medium red-purple colored flowers, dark green colored foliage, compact-globular growth habit. The new cultivar was discovered and selected as a single flowering plant within the progeny of the above stated cross-pollination during the summer of 2009 in a controlled environment in Boskoop, The Netherlands.

Asexual reproduction of the new cultivar by softwood cuttings since the summer of 2009 in Boskoop, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Odessa' as a new and distinct cultivar of *Spiraea* plant:

1. Deep rosy-pink colored flowers;
2. Dark green-colored foliage; and
3. Moderately vigorous, compact-globular growth habit.

Plants of the new cultivar differ from plants of the female parent primarily in flower color, foliage color, and in having a more compact growth habit. Plants of the new cultivar differ from plants of the male parent primarily in flower color and in having a more compact growth habit.

Of the many commercially available *Spiraea* cultivars, the most similar in comparison to the new cultivar is Lightning Strike 'Conalex', U.S. Plant Pat. No. 21,473. However, in comparison, plants of the new cultivar differ from plants of 'Conalex' in at least the following characteristics:

1. Plants of the new cultivar have a flower color different from plants of 'Conalex';
2. Plants of the new cultivar have a foliage color that is darker than plants of 'Conalex'; and
3. Plants of the new cultivar have a larger corolla diameter than plants of 'Conalex'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Odessa'. The plants were grown for two growing seasons outdoors in Boskoop, The Netherlands.

DETAILED BOTANICAL DESCRIPTION

Figure 1:
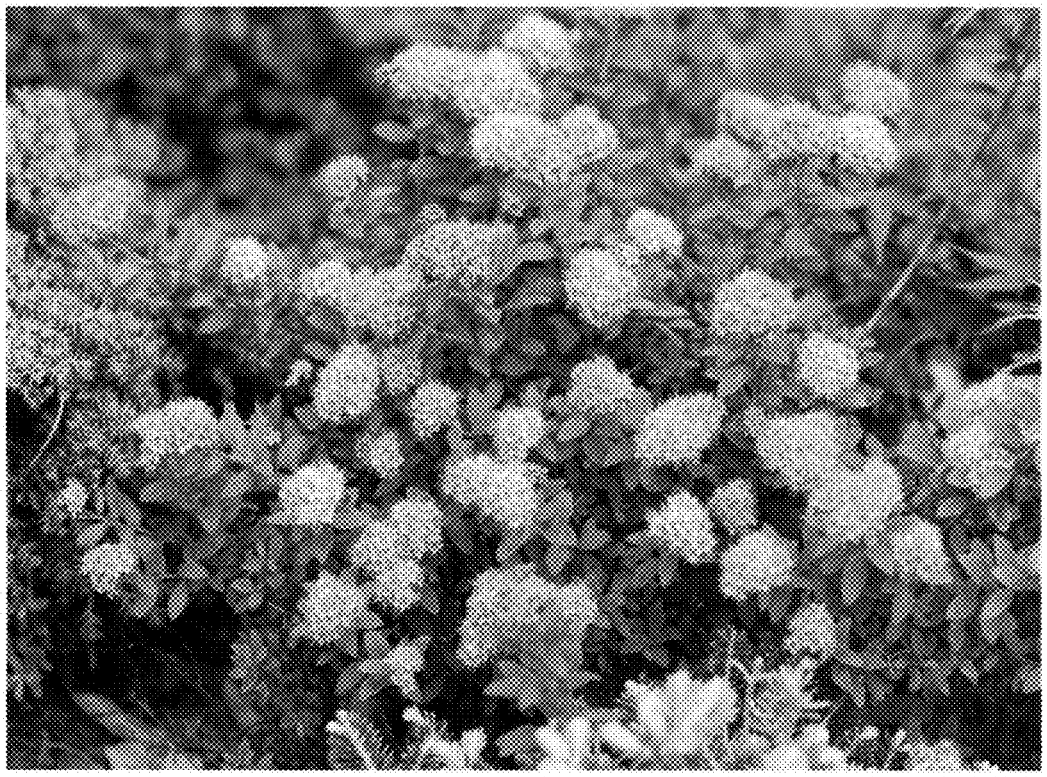
FIG. 1 illustrates a side view of the overall growth and flowering habit of 'Odessa'.
Figure 2:
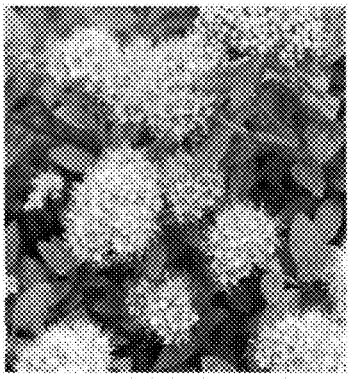
FIG. 2 illustrates a close-up view of inflorescences of 'Odessa'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in Boskoop, The Netherlands.

The following descriptions and measurements describe plants produced from cuttings from stock plants and grown under conditions comparable to those used in commercial practice. The plants were grown in 2-liter containers for approximately 2 growing seasons outdoors in Boskoop, The Netherlands. Average daily temperatures for the summer seasons ranged from approximately 60° F. to 82° F. (15° C. to 28° C.) and average night temperatures ranged from approximately 40° F. to 68° F. (4° C. to 20° C.). Average temperatures for the winter season ranged from approximately 40° F. to 50° F. (4° C. to 10° C.) with frosts to 12° F. (−11° C.). No supplemental lighting was provided. Measurements and numerical values represent averages of typical plants.

Botanical classification: *Spiraea japonica* cultivar Odessa.

Parentage:

*Female parent*.—'Little Princess', not patented.

*Male parent*.—'Bullata', not patented.

Propagation:

*Type cutting*.—Softwood.

*Time to initiate roots, summer*.—Approximately 25 days at 20° C.

*Time to produce a rooted cutting, summer*.—Approximately 25 days at 20° C.

*Root description*.—Fibrous, fine to thick, creamy white in color.

*Rooting habit*.—Freely branching, dense.

Plant description:

*Commercial crop time*.—Approximately 18 months from a rooted cutting to finish in a 20 cm pot.

*Growth habit and general appearance*.—Low mounding shrub, moderately vigorous, compact-globular.

*Size*.—Height from soil level to top of plant plane: Approximately 30.0 cm. Width: Approximately 30.0 cm.

*Branching habit*.—Freely basal branching, pinching not required. Aspect: Erect to 80° from center. Quantity of lateral branches: Approximately 15.

*Lateral branches*.—Strength: Strong. Length: Approximately 5.0 cm. Diameter: Approximately 5.0 mm. Length of central internode: Approximately 3.0 mm. Texture: Glabrous. Color of young stems: 149C. Color of mature stems: Woody, 199B.

Foliage description:

*General description*.—Fragrance: None detected. Form: Simple. Arrangement: Opposite.

*Leaves*.—Aspect: Acute angle to stem. Shape: Ovate. Margin: Serrate. Apex: Broadly acute. Base: Obtuse. Venation pattern: Pinnate. Length of mature leaf: Approximately 2.0 cm. Width of mature leaf: Approximately 1.0 cm. Texture of upper surface: Glabrous, moderately rugose. Texture of lower surface: Glabrous, ribbed. Color of upper surface of young foliage: N137A. Color of lower surface of young foliage: N138B. Color of upper surface of mature foliage: N137A with venation indistinguishable from leaf lamina. Color of lower surface of mature foliage: 138B with venation indistinguishable from leaf lamina.

*Petiole*.—Length: Approximately 2.0 mm. Diameter: Approximately 1.0 mm. Texture: Glabrous. Color: Upper surface N137A and lower surface N138B.

Flowering description:

*Flowering habit*.—'Odessa' is freely flowering under outdoor growing conditions with substantially continuous blooming from June through August.

*Lastingness of individual inflorescence on the plant*.—Approximately 20 to 25 days.

Inflorescence description:

*General description*.—Type: Compound corymbs. Aspect: Facing upward to slightly outward. Fragrance: Slightly sweet. Quantity per plant: Approximately 12. Diameter: Approximately 4.0 cm to 5.0 cm. Height: Approximately 3.0 cm.

*Peduncle*.—Strength: Strong. Shape: Triangular. Aspect: Mostly erect. Length: Approximately 3.0 cm to 4.0 cm. Diameter: Approximately 1.0 mm to 1.5 mm. Texture: Glabrous. Color: 145A.

Flower description:

*General description*.—Type: Single, rotate, not persistent. Aspect: Upright. Quantity per inflorescence: Approximately 130.

*Bud just before opening*.—Shape: Globose. Diameter: Approximately 2.0 mm. Color: 58A.

*Corolla*.—Diameter: Approximately 7.0 mm. Depth: Approximately 3.0 mm.

*Petals*.—Quantity: 5, in a single whorl. Shape: Orbicular. Margin: Entire. Apex: Rounded. Base: Obtuse. Length: Approximately 2.5 mm. Width: Approximately 2.0 cm. Texture of upper and lower surfaces: Glabrous. Color of upper surface when first open: 58B. Color of lower surface when first open: 58C. Color of upper surface when fully open: 57D. Color of lower surface when fully open: 57D.

*Calyx*.—Shape: Star-shaped. Diameter: Approximately 4.0 mm. Depth: Approximately 2.0 mm.

*Sepals*.—Quantity: 5. Arrangement: in a single whorl. Shape: Lanceolate. Margin: Entire. Length: Approximately 2.0 mm. Width: Approximately 1.0 mm. Apex: Acute. Base: Fused. Texture of inner and outer surfaces: Glabrous. Color of upper surface when first and fully open: 145A with an overlay of 187A. Color of lower surface when first and fully open: 145A with an overlay of 187A.

*Pedicles*.—Strength: Strong. Aspect: Erect. Length: Approximately 1.0 cm. Diameter: Approximately 1.0 mm. Texture: Glabrous. Color: 145A with an overlay of 187A.

*Reproductive organs*.—Androecium: Quantity per flower: 5. Stamen length: Approximately 3.5 mm. Filament length: Approximately 3.0 mm. Filament color: 58A. Anther shape: Globose. Anther length: Approximately 0.5 mm. Anther color: 62B. Pollen amount: Moderate. Pollen color: 79B. Gynoecium: Quantity per flower: 1 per flower. Pistil length: Approximately 3.0 mm. Stigma shape: Globose. Stigma length: Less than 1 mm. Stigma color: 58A. Style length: Less than 1 mm. Style color: 58A. Ovary length: Approximately 2.5 mm. Ovary color: 58A.

Seed and fruit production: Neither seed nor fruit production has been observed.

Disease and pest resistance: Resistance to pathogens and pests common to *Spiraea* has not been observed.

What is claimed is:

1. A new and distinct cultivar of *Spiraea* plant named 'Odessa', substantially as herein illustrated and described.

* * * * *